United States Patent [19]

Quadbeck-Seeger et al.

[11] 3,984,406
[45] Oct. 5, 1976

[54] PRODUCTION OF UNSUBSTITUTED OR SUBSTITUTED ISATOIC ANHYDRIDE

[75] Inventors: Hans-Jüergen Quadbeck-Seeger, Ludwigshafen; Peter Tonne, Neustadt, both of Germany

[73] Assignee: BASF Aktiengesellschaft, Ludwigshafen (Rhine), Germany

[22] Filed: Nov. 27, 1973

[21] Appl. No.: 419,411

[30] Foreign Application Priority Data
Nov. 28, 1972 Germany............................ 2258150
Sept. 14, 1973 Germany............................ 2346308

[52] U.S. Cl............................................. 260/244 A
[51] Int. Cl.² ............. C07D 265/00; C07D 273/00; C07D 295/00
[58] Field of Search........................ 260/244 A, 244

[56] References Cited
UNITED STATES PATENTS

| | | |
|---|---|---|
| 3,122,538 | 2/1964 | Clauson-Kaas et al. ........ 260/244 R |
| 3,383,415 | 5/1968 | Carabateas...................... 260/244 R |
| 3,509,198 | 4/1970 | Kuehle et al..................... 260/244 R |

FOREIGN PATENTS OR APPLICATIONS

| | | |
|---|---|---|
| 1,287,580 | 1/1969 | Germany......................... 260/244 R |
| 1,950,281 | 4/1971 | Germany |

*Primary Examiner*—James O. Thomas, Jr.
*Assistant Examiner*—D. W. Robinson
*Attorney, Agent, or Firm*—Johnston, Keil, Thompson & Shurtleff

[57] ABSTRACT

The production of unsubstituted or substituted isatoic anhydride by reaction of an alkali metal phthalamate with a hypohalite in the presence of bromine, iodine and/or a halogen amide or polymerization inhibitor. The products are starting materials for the production of dyes, plant protection agents and odorants.

12 Claims, No Drawings

PRODUCTION OF UNSUBSTITUTED OR SUBSTITUTED ISATOIC ANHYDRIDE

The invention relates to a process for the production of unsubstituted or substituted isatoic anhydride by reaction of an alkali metal salt of phthalamic acid with a hypohalite in the presence of bromine, iodine and/or a halogen amide or polymerization inhibitor.

It is known from German Pat. No. 127,138 that phthalimide can be reacted in alkaline solution with hypohalites to form isatoic anhydride. The difficulties which occur in the reaction, particularly the unsatisfactory yield and purity of the end product, are described by E. Mohr (J.Prakt.Chem. (2), volume 80 (1909), pages 1 to 33). Satisfactory operation of this method on a commercial scale is impossible.

Production of isatoic anhydride by reaction of phthalimide and hypohalites is described in German Printed Application (DAS) 1,287,580. The phthalimide is used in the form of an aqueous solution of a salt and the hypohalite is added before 50% of the phthalimide in the solution has been hydrolyzed. After the halite solution has been added 18,000 to 30,000 gram calories are liberated in the reaction solution before the solution is adjusted to a pH of from 5.5 to 9. It is known from German Laid-Open Specification (DOS) 1,770,458 that good yields of isatoic anhydride are obtained only when the solution of the salt of phthalamic acid used contains at least 5% of the alkali metal salt of phthalimide. The description and Examples disclose that phthalamic acid solutions which are devoid of phthalimide require for the degradation a large excess of alkali which decreases the yield of end product by the formation of anthranilic acid and anthranoylanthranilic acid. The presence of phthalimide or a salt thereof is detrimental. For one thing phthalimide has to be prepared from phthalic anhydride in a separate step of the process; and for another thing phthalimide has only limited stability in alkaline solution because it easily hydrolyzes into salts of phthalamic acid. The excess of alkali which has to be neutralized in the isolation of the end product presents waste water problems.

It is disclosed in German-Laid-Open Specification (DOS) 1,950,281 that isatoic anhydride can be prepared continuously by reaction of an alkali metal salt of phthalamic acid with a hypohalite in an aqueous medium by carrying out the first stage of the reaction under substantially adiabatic conditions and with substantial avoidance of backmixing, removing the reaction mixture formed immediately from the reaction chamber of the first stage and supplying it substantially without backmixing to the reaction chamber of the following stage, the reaction to form the end product. The process cannot be carried out batchwise even in small batches and is unsatisfactory as regards the yield of end product.

The object of the invention is a new process starting from an alkali metal phthalamate which is easier to prepare than phthalimide, for producing isatoic anhydride in a simpler and more economical manner and in some cases in a better yield and higher purity. The haloamide (I) has the formula

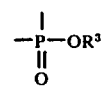
(I)

where $R^1$ is a sulfo group, a sulfonate radical or a sulfonamido group;
$R^2$ is hydrogen, chlorine or bromine;
X is chlorine, bromine or hydrogen;
$R^1$ and $R^2$ together with the adjacent nitrogen may be members of a heterocyclic radical having adjacent to the nitrogen atom at least one sulfonyl or phosphonyl group of the formula:

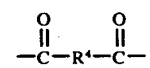

in which
$R^3$ is hydrogen or an alkali metal atom; or
$R^1$ and $R^2$ together may together form the radical

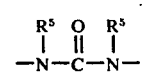

in which $R^4$ is alkylene, the radical

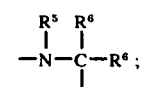

or the radical $$-\underset{\underset{|}{R^6}}{\overset{R^5}{|}}{N}-\underset{|}{\overset{|}{C}}-R^6 ;$$

$R^5$ is hydrogen, chlorine or bromine; and
$R^6$ is an aliphatic radical; or in the presence of a polymerization inhibitor.

When the sodium salt of phthalamic acid and sodium hypochlorite are used, the reaction may be represented by the following formulae:

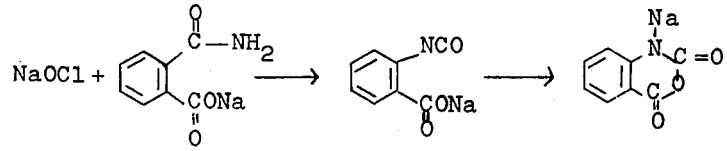

As compared with the prior art methods the process of the invention (starting from an alkali metal salt of phthalamic acid which is an easier starting material to prepare than phthalimide) gives isatoic anhydrides in a simpler and more economical way and in some cases in a better yield and purity. It is surprising having regard to the said patent specifications that good results are achieved by the process of the invention although the reaction with an alkali metal phthalamate alone and without hydrolysis of the phthalimide and/or adjustment of the pH is carried out using the conditions claimed in DAS 1,287,580. As compared with the process using alkali metal phthalamate as starting material the yield and purity of the end product are better. Since less salt occurs in the process of the invention and secondary reactions are hardly observable, there are fewer waste water problems.

The starting materials used are (a) an alkali metal phthalamate or an alkali metal salt of a substituted phthalamic acid (starting phthalamic salt) and (b) a hypohalite, as a rule a hypochlorite or hypobromite, in an aqueous medium, usually in the form of appropriate aqueous alkaline solutions. It is advantageous to use an aqueous solution of from 1 to 50% by weight of starting phthalamic acid (not including the alkali metal), which contains from 1 to 1.1 moles of alkali metal hydroxide per mole of phthalamic acid. Sodium hydroxide and potassium hydroxide are preferred.

The aqueous solutions of hypohalite generally contain from 5 to 15% and preferably from 12 to 14% by weight of hypohalite and may additionally contain from 0.01 to 0.1 mole of alkali metal hydroxide per mole of hypohalite. In the starting mixture there may be present in general a total amount of from 0.9 to 1.5 moles and preferably from 0.95 to 1.05 moles of hypohalite and optionally a total of from 0.01 to 0.2 mole of alkali metal hydroxide (not including the alkali metal contained in the hypohalite and in the starting phthalamate) for each mole of starting phthalamate.

The preferred hypohalites are hypochlorites and particularly alkali metal hypochlorites, for example the sodium or potassium salt, or alkaline earth metal hypochlorites, for example the calcium or magnesium salt.

Preferred isatoic anhydrides are those of the formula (II):

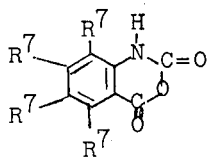

(II)

and consequently preferred starting phthalamates are potassium phthalamates and particularly sodium phthalamates of the formula (III):

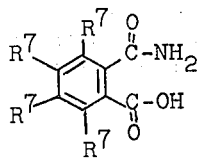

(III)

in which the individual radicals $R^7$ are identical or different and each is an aliphatic radical, preferably alkyl of one to four carbon atoms, hydrogen, halogen, preferably bromine and particularly chlorine, carboxyl or carboxylate, particularly alkali metal carboxylate such as sodium carboxylate or potassium carboxylate. Preferred starting materials bear not more than one carboxyl or alkali metal carboxylate and not more than one halogen apart from the carboxyl group and carbamide group required for the formation of the anhydride ring.

For example the salts of the following phthalamic acids are suitable as starting materials: phthalamic-(2) acid, 3-chlorophthalamic acid, 4-bromophthalamic acid, 3,5-dichlorophthalamic acid, 3,6-dichlorophthalamic acid, 3-carboxyphthalamic acid, 3- carboxy-6-chlorophthalamic acid, 3-methylphthalamic acid, 4-ethylphthalamic acid, 6-tert.-butylphthalamic acid, 4-sodium-carboxylatophthalamic acid and 4-n-propyl-5-chlorophthalamic acid.

Suitable catalysts include bromine, iodine and/or haloamides (I), generally in an amount of from 0.01 to 10 mole% and preferably from 0.1 to 1 mole% per mole of starting phthalamate and the polymerization inhibitors generally in an amount of from 0.01 to 20, advantageously from 0.01 to 10 and preferably from 0.01 to 2 mole% per mole of starting phthalamate.

Instead of the said substance use may be made of compounds which under the reaction conditions form such substances, for example bromides and iodides instead of bromine and iodine. Water-soluble halides are conveniently chosen. These halides are advantageously in the form of the alkaline earth metal salts and particularly the alkali metal salts, for example calcium bromide, calcium iodide, magnesium bromide, magnesium iodide, lithium bromide, lithium iodide and particularly sodium bromide, potassium bromide, sodium iodide and potassium iodide. When a hypobromite is used as the hypohalite the addition of a catalyst may be dispensed with because the bromine formed from the hypobromite under the reaction conditions serves as a catalyst. Preferred haloamides (I) are those in whose formula $R^1$ is a sulfo group, a sulfonate radical and particularly an alkali metal sulfonate radical such as sodium sulfonate or potassium sulfonate, or a sulfonamido group, $R^2$ is chlorine, bromine or particularly hydrogen, X is bromine, chlorine or advantageously hydrogen, $R^1$ and $R^2$ may also together with the adjacent nitrogen atom be members of a heterocyclic five-membered or six-membered ring which contains adjacent to the nitrogen at least one sulfone or phosphone group of the formula:

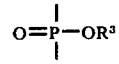

in which $R^3$ is hydrogen or alkali metal, particularly sodium or potassium, or $R^1$ and $R^2$ together may be

in which $R^4$ is alkylene of two to four carbon atoms,

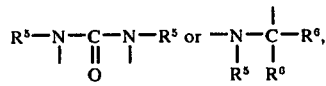

$R^5$ is hydrogen, chlorine or bromine and $R^6$ is alkyl of one to four carbon atoms and particularly methyl. A phenylene nucleus may be fused with the said heterocyclic ring. The heterocyclic ring advantageously contains adjacent to the nitrogen atom two sulfone or phosphone groups or two or three sulfonamido groups or phosphonamido groups, particularly in the same ring in the case of polynuclear heterocyclic radicals. The said preferred radicals may contain groups or atoms which are inert under the reaction conditions, for example chlorine, bromine, alkyl of one to four carbon atoms, or carboxyl or carboxylate as substituents on the phenyl nucleus.

Examples of catalysts are: glutarimide, adipimide, succinimide; preferably cyanuric acid, 5,5-dimethylhydantoin, trisulfamide, sodium triimidometaphosphate; and appropriate mixtures of the said haloamides (I); particularly preferred are sulfamic acid and salts thereof, advantageously alkali metal salts such as the sodium or potassium salt, and sulfamide, if desired mixed with the said haloamides (I).

The polymerization inhibitors used are substances which prevent or markedly retard the polymerization of monomers and thus act as stabilizers with regard to the monomers. The substances may be gaseous, solid or liquid and those are preferred which inhibit the polymerization of vinyl compounds, and particularly those which inhibit free radical polymerization. It is advantageous to use as inhibitors: sodium nitrate or inorganic compounds of divalent sulfur, preferably hydrogen sulfide, alkali metal sulfides, for example sodium sulfide or potassium sulfide, alkali or alkaline earth metal hydrogen sulfides, for example lithium hydrogen sulfide, sodium hydrogen sulfide, potassium hydrogen sulfide, ammonium sulfide and ammonium polysulfide. Compounds which contain only some of the sulfur in the molecule in divalent form, such as alkali metal thiosulfates, for example sodium thiosulfate, may also be used. Phenol and thiophenol are also convenient catalysts.

Particularly advantageous catalysts include, among the polymerization inhibitors, nitrogen compounds of the formula (IV):

$$R^{10}-\underset{\underset{R^9}{|}}{\overset{\overset{R^8}{|}}{N}}-R^9 \quad (IV)$$

in which $R^8$ is an aliphatic radical, preferably alkyl of one to four carbon atoms, a six-membered heterocyclic radical containing three nitrogen atoms and particularly a triazinyl radical bearing amino groups as substituents,

in which $R^{11}$ is an aliphatic radical and particularly alkyl of one to four carbon atoms,

(in which $R^{12}$ is hydrogen or cyano), cyano, sulfonyl chloride, sulfo,

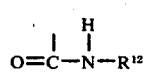

(where $R^{12}$ is an aliphatic radical and particularly alkyl of one to four carbon atoms, an araliphatic radical and particularly aralkyl of seven to twelve carbon atoms, amino or cycloalkylamino and particularly cyclohexylamino), sulfonate and particularly alkali sulfonate such as sodium sulfonate or potassium sulfonate, $R^9$ is an aliphatic radical and preferably alkyl of one to four carbon atoms, hydrogen,

(in which $R^{12}$ is hydrogen or cyano), phenyl or cyclohexyl, $R^{10}$ is an aliphatic radical and preferably alkyl of one to four carbon atoms, chlorine, bromine or particularly hydrogen, $R^8$ and $R^9$ may also together with the adjacent nitrogen be members of a five-membered or six-membered heterocyclic ring which may contain an oxygen atom or an oxo group or the radical

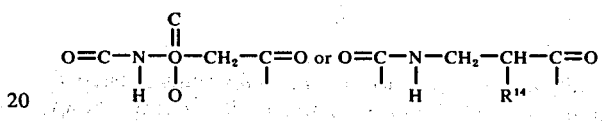

(in which $R^{14}$ is alkyl of one to four carbon atoms), or $R^8$, $R^9$ and $R^{10}$ together with the adjacent nitrogen may form a bicyclic or tricyclic radical which may contain one to three nitrogen atoms and preferably a bicyclic or tricyclic radical of two to four nitrogen atoms and three to six carbon atoms. The said preferred rings and radicals may bear groups which are inert under the reaction conditions, for example alkyl of one to three carbon atoms, as substituents. The rings may contain double bonds. The nitrogen compounds may also be used in the form of their salts, for example p-toluenesulfamide in the form of chloramine-T.

Particularly preferred catalysts for the reaction include:
diazabicyclo-[2,2,2]-octane

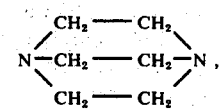

sodium thiosulfate, phenol, thiophenol, melamine

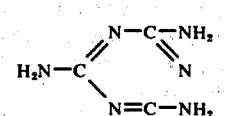

urea, cyanourea

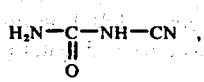

trimethylamine, N,N'-dicyclohexylsulfamide $C_6H_{11}$-NH-$SO_2$-NH-$C_6H_{11}$, sodium hydrogen sulfide, thymine

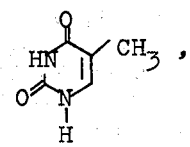

acetanilide, ethylurethane

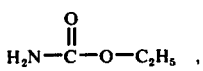

n-propylaminosulfochloride, biuret $NH_2\text{-}CO\text{-}NH\text{-}CO\text{-}NH_2$, isopropylaminosulfonic acid $(CH_3)_2\text{-}CH\text{-}NH\text{-}SO_3H$, urotropine, cyanamide $H_2N\text{-}C \equiv N$, p-toluenesulfamide, pyrrolidone, barbituric acid

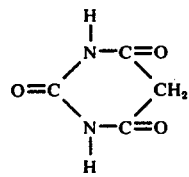

N-ethylacetamide, morpholine, piperidine, triethylamine, n-butylsulfamide, methanesulfonamide, chloramine-T,

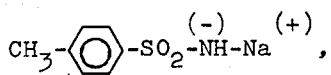

sodium nitrite.

The reaction is carried out as a rule at a temperature of from −30° to +80°C, advantageously from 0° to 80°C and preferably from 0° to 40°C, at atmospheric or superatmospheric pressure, continuously or batchwise. The reaction may be carried out as follows: a mixture of the starting phthalamate, catalyst and water has added to it an aqueous solution of a hypohalite and the mixture is kept at the reaction temperature for from 1 second to 100 minutes and particularly from 1 second to 1000 seconds. The end product is then isolated by a conventional method, for example by neutralization of the reaction mixture with a suitable acid such as sulfuric acid followed by filtration.

The catalyst, conveniently mixed with water, may also be added to the starting mixture separately or with the hypohalite. The higher the reaction temperature chosen the shorter should expediently be the reaction period up to the time when acid is added. In a preferred embodiment which at the same time illustrates the particularly simple and advantageous operation of plant using the process of the invention the starting phthalamate is first prepared from phthalic anhydride, ammonia and alkali metal hydroxide at a temperature as a rule of from 20° to 80°C and the reaction mixture thus formed is reacted direct without isolation of the reaction product as the starting material for the process of the invention.

The compounds which can be prepared by the process of the invention are valuable starting materials for the production of dyes, plant protection agents and odorants. The isatoic anhydrides may be converted by hydrolysis with alkali into the equivalent anthranilic acids. Information concerning use of the compounds may be found in the said patent specifications and Ullmanns Encyklopadie der technischen Chemie, volume 3, pages 465 et seq. and volume 13, page 499.

The following Examples illustrate the invention. Parts specified are by weight. They bear the same relation to parts by volume as the kilogram to the liter.

EXAMPLE 1 a. 60.2 parts of phthalic anhydride is added to a mixture (at 25°C) of 84 parts by volume of water and 60.5 parts by volume of 25% by weight aqueous ammonia solution. The solution is cooled (pH from 7.5 to 8.0) to 40°C and another 60.2 parts of phthalic anhydride and 68 parts by volume of 35% by weight aqueous caustic soda solution are added. The temperature rises to 75°C and a clear solution is obtained. The mixture is then cooled to 10°C.

b. a solution at 25°C of 480 parts by volume of water and 78 parts by volume of hypochlorite solution (containing 13.2 parts of sodium hypohalite) is added at 25°C to a solution of 62 parts by volume of the solution from Example 1(a), 60 parts by volume of water and 0.2 part of sulfamide. After 12 seconds at 33°C 15 parts by volume of 25% by weight aqueous sulfuric acid is added and the mixture is stirred for another 5 minutes. The mixture is then suction filtered and the filtered material is washed and dried in vacuo at 60°C. The yield is 25.7 parts (99.5% by weight) of isatoic anhydride having the decomposition point 235°C, corresponding to 91.4% of theory.

EXAMPLE 2

A solution at 25°C of 480 parts by volume of water and 78 parts by volume hypochlorite solution (with a content of 13.2 parts of sodium hypohalite) is added to a mixture of 62 parts by volume of the solution from Example 1(a), 60 parts by volume of water and 1 part of sodium iodide at 25°C. Fifteen seconds later at 33°C 15 parts by volume of 25% by weight aqueous sulfuric acid is added and the whole is stirred for 5 minutes. The mixture is then suction filtered and the filter cake is washed and dried. The yield is 26.1 parts (99.7% by weight) of isatoic anhydride of the decomposition point 235°C, corresponding to 93% of theory.

EXAMPLE 3

1540 parts of a 5.1% by weight aqueous solution of sodium phthalamate (to which 0.4 part of sulfamic acid has been added) and 225 parts of hypochlorite solution (containing 31.5 parts of sodium hypohalite) are fed per hour continuously by means of metering pumps to a mixing unit (mixing temperature 25°C) and brought to reaction in a tubular reactor downstream thereof at 25°C. The clear solution flows after a dwell period of 12 seconds into a stirred vessel in which it is neutralized by continuous metering in of 85 parts per hour of 25% by weight aqueous sulfuric acid. The suspension of isatoic anhydride which is at 45°C is passed continuously through a suction filter. A mean residence time of 10 minutes is maintained in the neutralization vessel. After washing for a short time the moist isatoic anhydride may be further processed. 63.5 parts per hour of isatoic anhydride of the decomposition point 235°C is obtained; this is equivalent to 92.4% of theory.

EXAMPLE 4 a. 9.1 parts of 4-chlorophthalic anhydride is introduced into a mixture of 90 parts by volume of water and 7.5 parts by volume of 25% by weight aqeuous ammonia solution. The solution (pH about 8) has another 9.1 parts of 4-chlorophthalic anhydride and 6.0 parts by volume of 50% by weight aqueous caustic soda solution added to it. The clear solution is cooled to 25°C.

b. 0.1 part of sulfamide is added to the solution from Example 4(a) and then in one portion a solution of 47 parts by volume of hypochlorite solution (containing 7.5 parts of sodium hypohalite) and 70 parts by volume of water is then added. After 4 seconds at 29°C the mixture is adjusted to pH 7 with 2 parts by volume of 25% by weight aqueous sulfuric acid. The mixture is stirred for another 30 minutes, suction filtered and the filter cake is washed and dried in vacuo at 60°C. The yield is 17 parts (98.8% by weight) chloroisatoic anhydride of the decomposition point 196° to 204°C, equivalent to 85.1% of theory.

EXAMPLE 5 a. 6.4 parts of trimellitic anhydride is added to a mixture of 150 parts by volume of water and 9.5 parts by volume of 20% by weight aqueous ammonia solution. Another 12.8 parts of trimellitic anhydride and 12 parts by volume of 50% by weight aqueous caustic soda solution are introduced into the solution. The clear solution is cooled to 5°C.

b. 0.2 part of sulfamic acid is added to the solution from Example 5(a) followed all at once by a solution of 45 parts by volume of aqueous hypochlorite solution (containing 7.5 parts of sodium hypohalite) and 100 parts by volume of water at 5°C. After thirty seconds the mixture is adjusted to pH 7.5 with 25% by weight aqueous sulfuric acid and stirred for another ten hours. The mixture is suction filtered and the filter cake is washed with a small amount of water and dried in vacuo at 40°C. The yield is 19.2 parts of (98% by weight) sodium salt of the carboxylisatoic anhydride having a melting point above 320°C, equivalent to 82% of theory.

EXAMPLE 6 a. 60.2 parts of phthalic anhydride is added to a mixture at 25°C of 84 parts by volume of water and 60.5 parts by volume of 25% by weight aqueous ammonia solution. The solution (pH 7.5 to 8.0) is cooled to 40°C and another 60.2 parts of phthalic anhydride and 68 parts by volume of 35% by weight aqueous caustic soda solution are added. The temperature rises to 75°C and a clear solution is obtained. The mixture is then cooled to 10°C.

b. A solution at 25°C of 480 parts by volume of water and 78 parts by volume of hypochlorite solution (containing 13.2 parts of sodium hypohalite) is added to a solution of 62 parts by volume of the solution from Example 1(a), 60 parts by volume of water and 2.4 parts of sodium thiosulfate at 25°C. After 60 seconds at 33°C 15 parts by volume of 25% by weight aqueous sulfuric acid is added and the mixture is stirred for 5 minutes at pH 7. The mixture is then suction filtered and the filter cake is washed and dried. The yield is 21.8 parts of (99.8% by weight) isatoic anhydride of the decomposition point 235°C, equivalent to 75% of theory.

EXAMPLES 7 TO 34

As described in Example 6 the catalysts and reaction periods (reckoned from the production of the starting mixture to the addition of the acid) set out in the following Table are used. In Examples 14 and 15 the catalyst is added to the hypochlorite solution. The following abbreviations are used in the Table: E = Example; RPS = reaction period in seconds; Y% = yield in % of theory.

Table

| E | Parts | Catalyst | RPS | Y% |
|---|---|---|---|---|
| 7 | 1.74 | diazabicyclo[2,2,2]octane | 10 | 88 |
| 8 | 1.04 | sodium nitrite | 30 | 41 |
| 9 | 1.41 | phenol | 45 | 52 |
| 10 | 1.65 | thiophenol | 40 | 57 |
| 11 | 1.9 | melamine | 90 | 82 |
| 12 | 0.9 | urea | 50 | 61 |
| 13 | 1.3 | cyanourea | 20 | 78 |
| 14 | 0.88 | trimethylamine | 100 | 76 |
| 15 | 3.66 | N,N'-dicyclohexylsulfamide | 60 | 81 |
| 16 | 0.84 | sodium hydrogen sulfide | 65 | 77 |
| 17 | 1.9 | thymine | 25 | 85 |
| 18 | 2.04 | acetanilide | 60 | 73 |
| 19 | 1.36 | ethylurethane | 25 | 59 |
| 20 | 2.36 | n-propylaminosulfochloride | 50 | 72 |
| 21 | 1.55 | biuret | 20 | 65 |
| 22 | 2.08 | isopropylaminosulfonic acid | 45 | 51 |
| 23 | 2.1 | protropine | 120 | 37 |
| 24 | 0.63 | cyanamide | 110 | 33 |
| 25 | 2.57 | p-toluenesulfamide | 80 | 35 |
| 26 | 1.28 | pyrrolidone | 180 | 38 |
| 27 | 1.92 | barbituric acid | 35 | 48 |
| 28 | 1.25 | N-ethylacetamide | 80 | 39 |
| 29 | 1.3 | morpholine | 80 | 33 |
| 30 | 1.28 | piperidine | 95 | 31 |
| 31 | 1.5 | triethylamine | 90 | 50 |
| 32 | 2.28 | n-butylsulfamide | 40 | 35 |
| 33 | 1.42 | methanesulfonamide | 50 | 43 |
| 34 | 2.9 | chloramine-T | 25 | 38 |

We claim:

1. A process for the production of an isatoic anhydride of the formula (II):

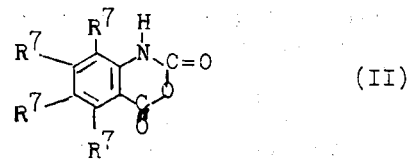

in which the individual radicals $R^7$ are identical or different and each is an alkyl of one to four carbon atoms, hydrogen, bromine, chlorine, carboxyl or alkali metal carboxylate wherein an alkali metal salt of a phthalamic acid of the formula (III):

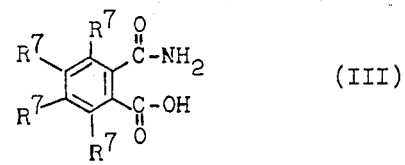

is reacted at −30° to +80°C with 0.9 to 1.5 moles, per mole of said phthalamate, of a hypochlorite in an aqueous alkaline solution in the presence of 0.01 to 10 mole percent, per mole of said phthalamate, of a catalyst selected from the group consisting of bromine and iodine.

2. A process as claimed in claim 1 wherein said aqueous alkaline solution contains 5–15% by weight of said hypochlorite.

3. A process as claimed in claim 1 wherein the reaction temperature is in the range of 0°–40°C.

4. A process as claimed in claim 1 wherein said mole percent of said catalyst is in the range of 0.1 to 1 mole percent per mole of said phthalamate.

5. A process for the production of an isatoic anhydride of the formula (II):

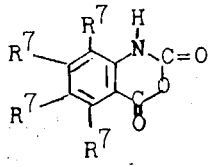

(II)

in which the individual radicals R⁷ are identical or different and each is an alkyl of one to four carbon atoms, hydrogen, bromine, chlorine, carboxyl or alkali metal carboxylate wherein an alkali metal salt of a phthalamic acid of the formula (III):

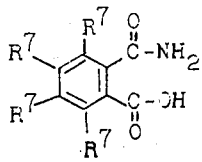

(III)

is reacted at −30° to +80°C with 0.9 to 1.5 moles, per mole of said phthalamate, of a hypochlorite in an aqueous alkaline solution in the presence of 0.01 to 10 mole percent per mole of said phthalamate of a catalyst selected from the group consisting of sulfamide, sulfamic acid, and an alkali metal salt of sulfamic acid.

6. A process as claimed in claim 5 wherein said aqueous alkaline solution contains 5–15% by weight of said hypochlorite.

7. A process as claimed in claim 5 wherein the reaction temperature is in the range of 0°–40°C.

8. A process as claimed in claim 5 wherein said mole percent of said catalyst is in the range of 0.1 to 1 mole percent per mole of said phthalamate.

9. A process for the production of an isatoic anhydride of the formula (II):

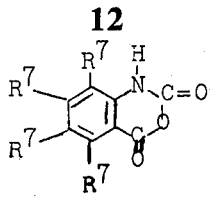

(II)

in which the individual radicals R⁷ are identical or different and each is an alkyl of one to four carbon atoms, hydrogen, bromine, chlorine, carboxyl or alkali metal carboxylate wherein an alkali metal salt of a phthalamic acid of the formula (III):

(III)

is reacted at −30° to +80°C with 0.9 to 1.5 moles, per mole of said phthalamate, of a hypochlorite in an aqueous alkaline solution in the presence of 0.01 to 20 mole percent per mole of said phthalamate of a polymerization inhibitor selected from the group consisting of diazabicyclo [2,2,2] octane, phenol, thiophenol, sodium thiosulfate, melamine, urea, cyanourea, trimethylamine, N,N'-dicyclohexylsulfamide, sodium hydrogen sulfide, thymine, acetanilide, ethylurethane, n-propylaminosulfochloride, biuret, isopropylaminosulfonic acid, urotropine, cyanamide, p-toluene-sulfamide, pyrrolidone, barbituric acid, N-ethylacetamide, morpholine, piperidine, triethylamine, n-butylsulfamide, methanesulfonamide, chloroamine-T and sodium nitrate.

10. A process as claimed in claim 9, wherein said aqueous alkaline solution contains 5–15% by weight of said hypochlorite.

11. A process as claimed in claim 9 wherein the reaction temperature is in the range of 0–40°C.

12. A process as claimed in claim 9 wherein said mole percent of said polymerization inhibitor compound is in the range of 0.1 to 10 mole percent per mole of said phthalamate.

* * * * *